United States Patent [19]

Grim

[11] Patent Number: 4,993,409
[45] Date of Patent: Feb. 19, 1991

[54] BACK SUPPORT

[75] Inventor: Tracy E. Grim, Broken Arrow, Okla.

[73] Assignee: Royce Medical Company, Westlake Village, Calif.

[21] Appl. No.: 308,687

[22] Filed: Feb. 8, 1989

[51] Int. Cl.⁵ ............................................. A61F 5/02
[52] U.S. Cl. ...................................... 128/78; 128/68
[58] Field of Search ............ 128/78, 68, 384, 399–402, 128/DIG. 20, 24.1, 24 R, 68.1; 5/431–433, 450

[56] References Cited

U.S. PATENT DOCUMENTS

| | | |
|---|---|---|
| 1,646,590 | 10/1927 | Mildenberg . |
| 2,554,337 | 5/1951 | Lampert ................................ 128/96 |
| 3,014,117 | 12/1961 | Madding .............................. 128/403 |
| 3,071,133 | 1/1963 | Eisen ........................................ 128/ |
| 3,071,133 | 1/1968 | Eisen ..................................... 128/78 |
| 3,419,702 | 12/1968 | Piel ........................................ 219/211 |
| 3,521,623 | 7/1970 | Nichols et al. ......................... 128/78 |
| 3,548,420 | 12/1970 | Spence ...................................... 128/ |
| 3,548,819 | 5/1968 | Davis ..................................... 128/82 |
| 3,561,435 | 2/1971 | Nicholson .............................. 128/87 |
| 3,780,537 | 12/1973 | Spencer ................................... 62/530 |
| 3,885,403 | 5/1975 | Spencer ................................... 62/530 |
| 3,901,225 | 8/1975 | Sconce .......................... 128/DIG. 20 |
| 3,974,827 | 8/1976 | Bodeen ......................... 128/DIG. 20 |
| 4,135,503 | 1/1979 | Romano ................................. 128/78 |
| 4,175,548 | 11/1979 | Henry ..................................... 128/24 |
| 4,178,922 | 12/1979 | Curlee .................................... 128/78 |
| 4,475,543 | 10/1984 | Brooks et al. .......................... 128/78 |
| 4,552,135 | 11/1985 | Racz et al. ............................. 128/78 |
| 4,572,167 | 2/1986 | Brunswick .............................. 128/78 |
| 4,576,169 | 3/1986 | Williams ............................... 128/403 |
| 4,597,384 | 7/1986 | Whitney ...................... 128/DIG. 20 |
| 4,597,386 | 7/1986 | Goldstein .............................. 128/78 |
| 4,622,957 | 11/1986 | Curlee .................................... 128/78 |
| 4,628,945 | 12/1986 | Johnson ............................ 128/80 H |
| 4,682,587 | 7/1987 | Curlee .................................... 128/78 |
| 4,682,588 | 7/1987 | Curlee .................................... 128/78 |
| 4,702,235 | 10/1987 | Hong ...................................... 128/78 |
| 4,756,306 | 7/1988 | Curlee .................................... 128/78 |
| 4,777,346 | 10/1988 | Swanton .............................. 128/403 |

FOREIGN PATENT DOCUMENTS

| | | | |
|---|---|---|---|
| 1461408 | 11/1966 | France . | |
| 2425239 | 12/1979 | France ............................. 128/118.1 |
| 985591 | 3/1965 | United Kingdom ............ DIG. 20/ |

Primary Examiner—Edgar S. Burr
Assistant Examiner—Huong Q. Pham
Attorney, Agent, or Firm—Poms, Smith, Lande & Rose

[57] ABSTRACT

The back support is constructed from a back brace of elastic material which carries a gel pad and an air bladder. The brace supports the pad against lower back of the user in firm engagement. The air bladder is juxtaposed and generally co-extensive with the pattern containing the gel-like material. The air bladder has three individually inflatable chambers so that the user may adjust the pressure exerted on the pad and hence the support of the lower back. The gel pad may also contain a heating element to electrically heat the gel-like material. A rheostat may be provided for regulation of the heat.

17 Claims, 5 Drawing Sheets

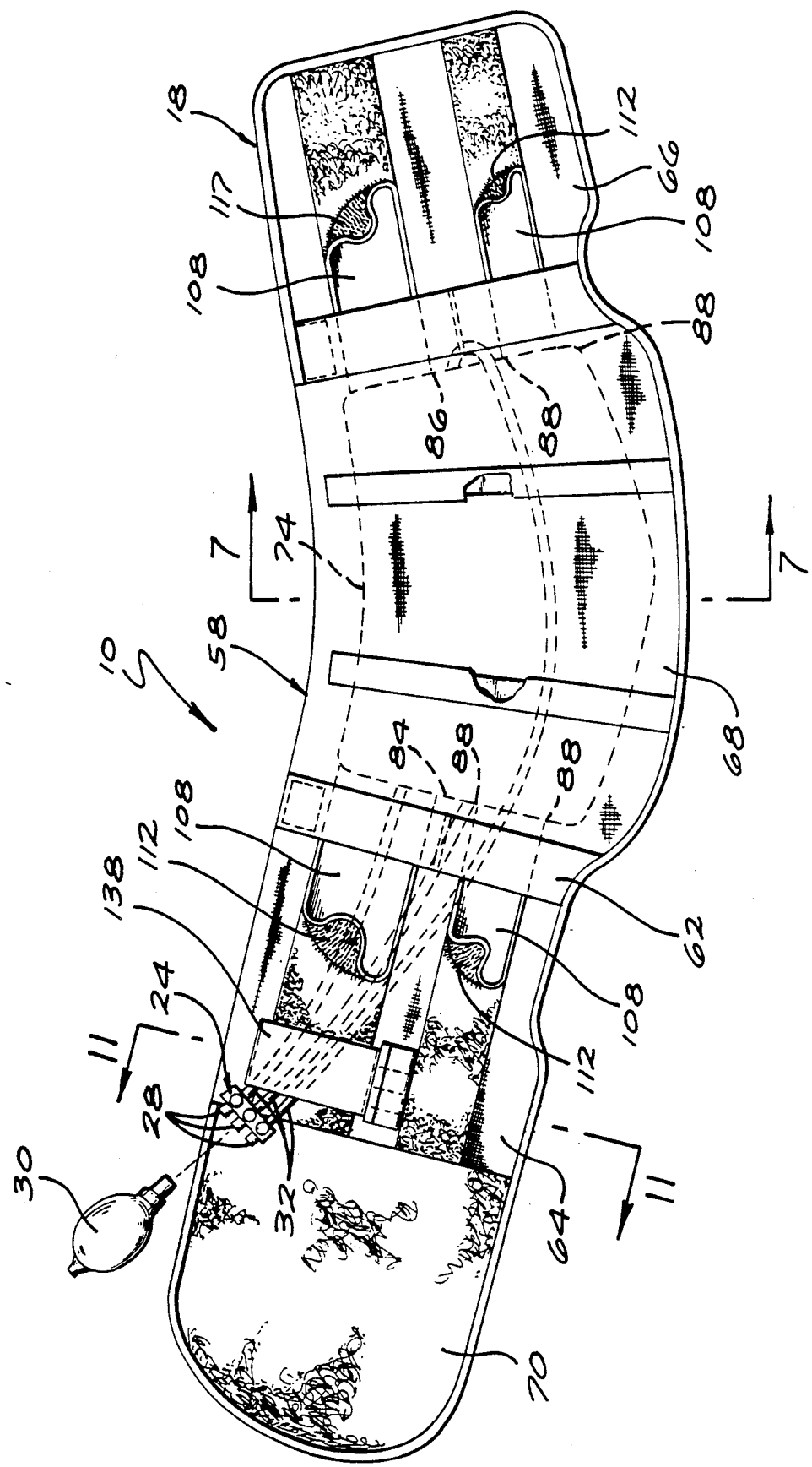

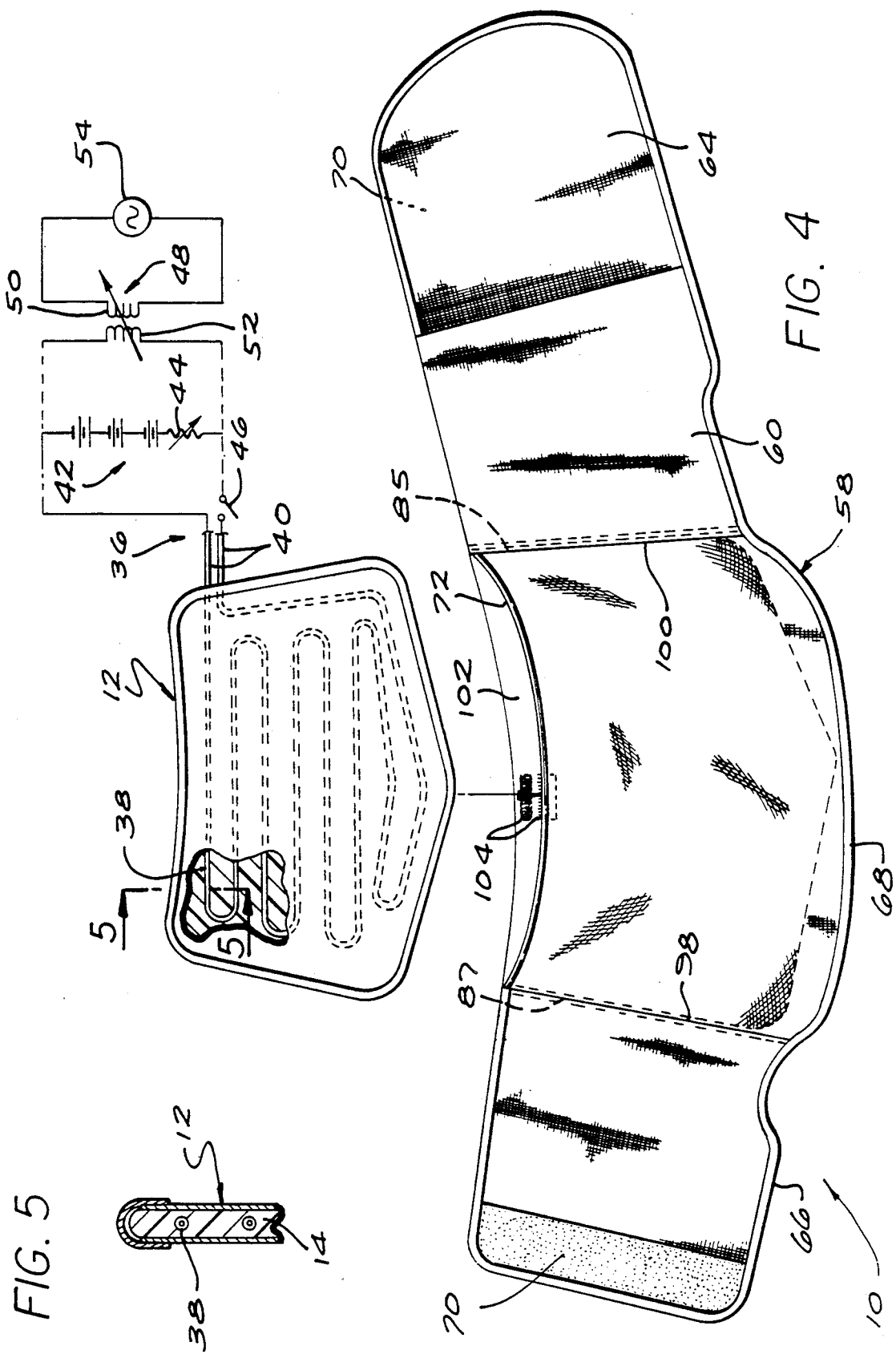

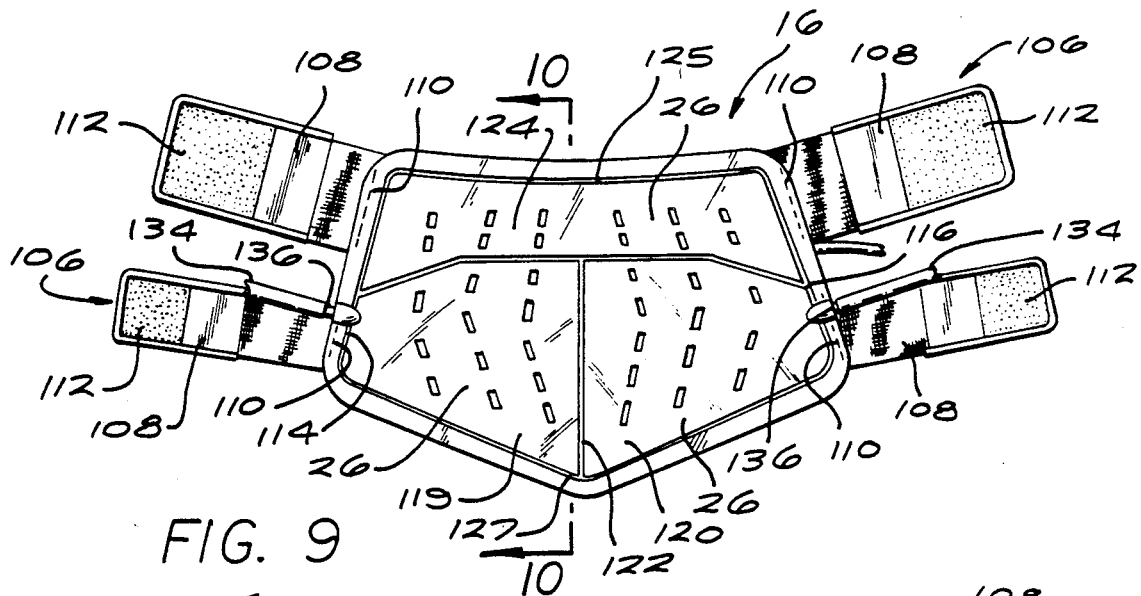
FIG. 8
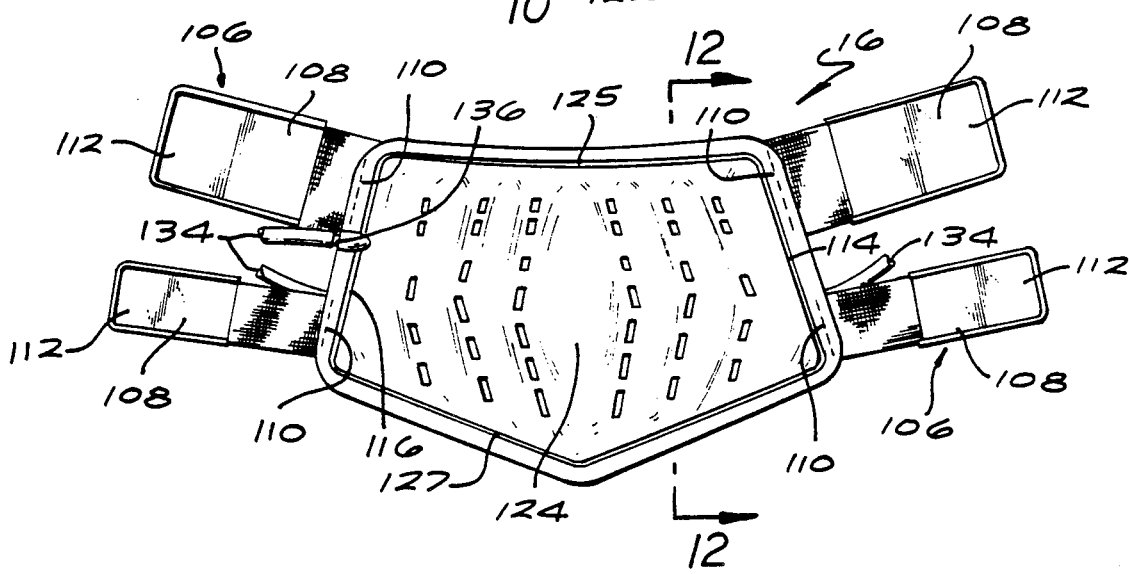
FIG. 9
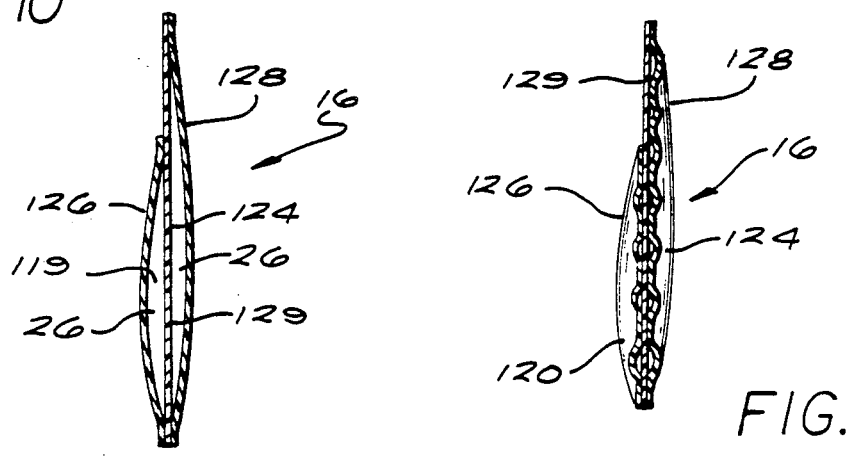
FIG. 10
FIG. 12

BACK SUPPORT

BACKGROUND OF THE INVENTION

1. Field of the Invention

This application for letters patent is related to copending application Serial No. 07/308,689, filed Feb. 8, 1989.

The present invention relates generally to back supports, and more particularly, to a novel back support having a gel pad and an inflatable bladder to press the gel pad against the lower back of the user.

2. Description of the Related Art

Back supports having air inflatable bladders are known. For example, U.S. Pat. No. 4,622,957 (Curlee), discloses a therapeutic corset having an elongated support surface formed from material which is bendable when subjected to forces encountered thereby. A flexible cover is disposed on the support surface and secured thereto along its edges to form an envelope. The envelope has a plurality of cells, such that when the envelope is inflated, it assumes a predetermined curvature such as a crescent.

When the corset is secured around a user, the envelope is held adjacent the sacrum lumbar and thoracic region of the body. Since the corset is formed from a relatively inelastic belting material, inflation of the envelope will exert a force against the above-mentioned body region.

The envelope as described above has a plurality of vertical ribs which form the series of intercommunicating inflatable cells. The vertical ribs cause the envelope to shrink thereby insuring the tabular ribs always conform to the anatomy during a full range of movement. For example, see U.S. Pat. No. 4,682,587 (Curlee) which discloses one such envelope and U.S. Patent No. 4,682,588 (Curlee) which discloses a vertical stack interconnected envelopes.

A disadvantage and limitation of the above devices is that the inflatable envelope is secured adjacent the body by relatively inelastic belting material. Such belting material if improperly secured about the torso may shift in position negating the therapeutic effects of the corset, and also causing discomfort to the wearer.

In the treatment of spinal disorder, it is also desirable to use hot or cold therapy in conjunction with the support provided by a back brace. The devices described above in reference to the Curlee patents do not disclose such therapy.

It is accordingly an object of the present invention to overcome one or more of the limitations and disadvantages of the prior art above enumerated. It is another object of the present invention to provide a back brace adaptable for hot or cold therapy and adjustable by air inflation.

SUMMARY OF THE INVENTION

According to the present invention, a back support includes the first pad having a gel-like substance contained therein and an air bladder co-extensive with a juxtaposed the gel pad. The back support further includes means for supporting the gel pad in firm engagement against the lower back of a user and means for inflating the air bladder to press the pad against the lower back. The gel pad may further be removed for heating or cooling and reinserted prior to use for hot or cold therapy.

One particular embodiment of the present invention, the air bladder has three chambers so that the user could adjust the pressure applied on the back according to the contours of the user's back.

In another embodiment of the present invention, the back support further includes an electrical heating disposed within the gel pad. External power either from a battery pack or from a wall outlet may supply current to the heating element. In the case of wall power current being used, a variable transformer allows the user to adjust the current in the heating element to adjust temperature.

These an other objects, advantages and features of the present invention will become apparent to those skilled in the art from a study of the following description of an exemplary preferred embodiment when read in conjunction with the attached drawings and appended claims.

BRIEF DESCRIPTION OF THE DRAWINGS

FIG. 3 is an elevational view, partially in phantom, of the back support shown in FIGS. 1 and 2.

FIG. 4 is an exploded elevational view of the back support of FIGS. 1 and 2;

FIG. 5 is a cross-sectional view taken along line 5—5 of FIG. 4;

FIG. 8 is an elevational view of the air bladder used in the back support of FIGS. 1 and 2;

FIG. 9 is an elevational view of the opposite side of the air bladder shown in FIG. 8;

FIG. 10 is a cross-sectional view taken along line 10—10 of FIG. 8; and

FIG. 12 is a cross sectional view taken along line 12—12 of FIG. 9.

DESCRIPTION OF THE PREFERRED EXEMPLARY EMBODIMENT

Figure 7:
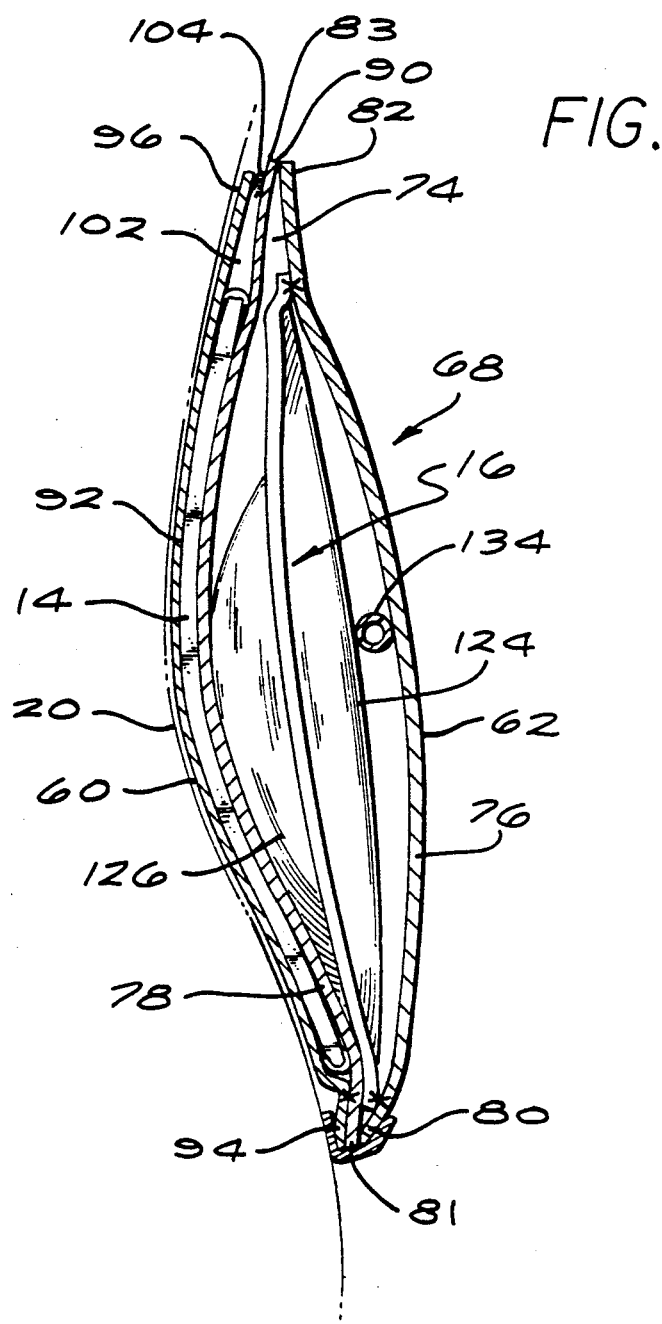
FIG. 7 is cross-sectional view taken along line 8—8 of FIG. 3.

Referring now to FIGS. 1-4, there is shown a back support 10 constructed according to the principles of the present invention. Back support 10 includes a pad 12 having a gel-like material 14 contained therein as best seen in FIG. 5 and FIG. 7, an air bladder 16, best seen in FIGS. 8-9, co-extensive with and juxtaposed to the pad 12, means 18 for supporting the pad 12 in firm engagement against the lower back 20 of a user 22, and means 24 for inflating the air bladder 16 to press the pad 12 against the lower back 20. The pad 12 of the gel-like material 14 is generally constructed from two sheets of vinyl which are sealed along the peripheral edges. The gel material 14 may be any conventional orthopedic gel, such as Elasto Gel commercially available from Technologies Inc. of Kansas City, Mo. For a comfort to the user, the gel pad may be jacketed by a soft cloth (not shown).

The air bladder 16 includes a plurality of chambers 26 as best seen in FIG. 8 and FIG. 10. Each of the chambers 26 are individually inflatable, as set forth in greater detail hereinbelow, by the inflating means 24.

Figure 1:
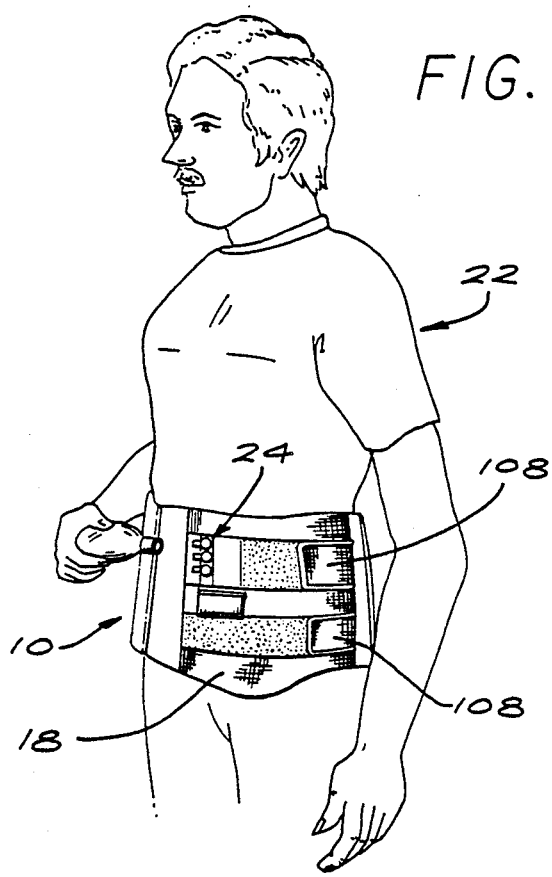
FIGS. 1 and 2 illustrate an intended use of a back support constructed according to the principles of the present invention.
Figure 2:
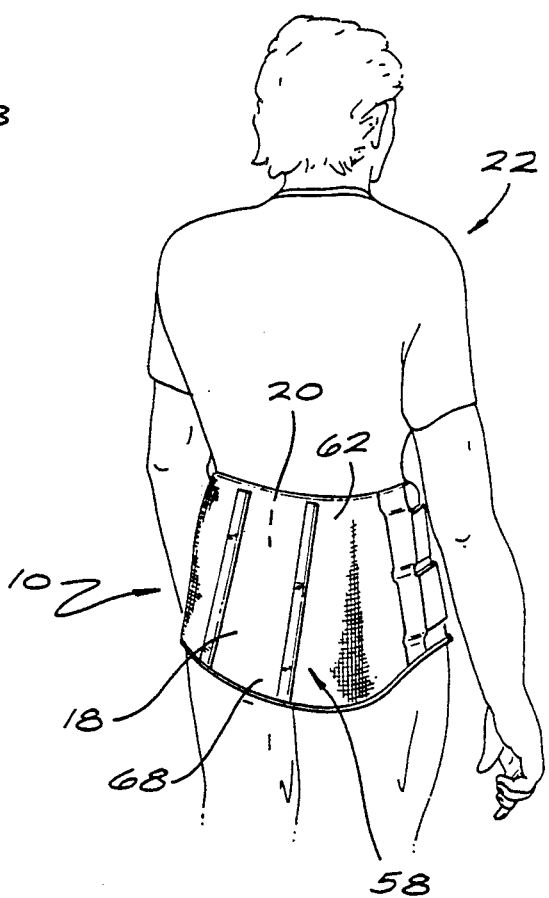
Figure 6:
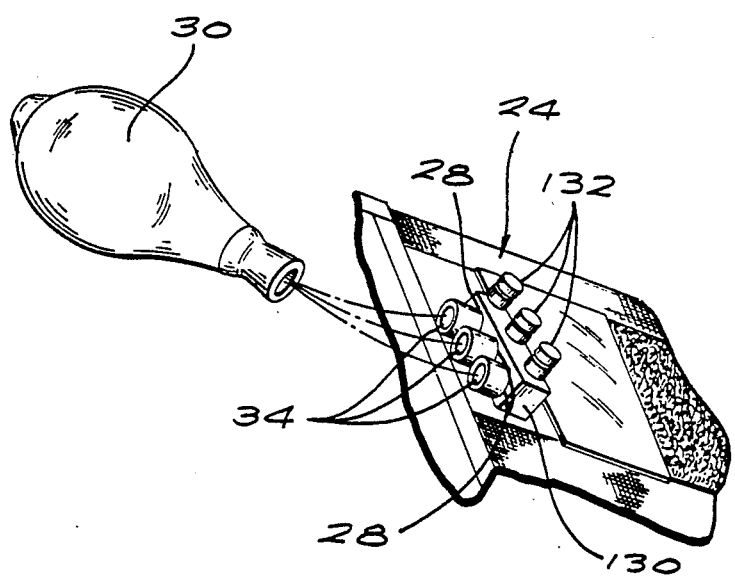
FIG. 6 is a enlarged prospective view of a portion of the back support shown in FIG. 3.

Inflating means 24 includes a plurality of one-way valves 28 and an air pump 30 as best seen in FIG. 3 and FIG. 6. Each of the one-way valves 28 has an outlet 32 operatively communicating with the respective one of the chambers 26 of the air bladder 16 and an inlet 34. The air pump 30 is adapted for coupling to the inlet 34 of a user selected one of the one-way air valve 28. The air pump 30 may be a conventional squeeze ball.

Figure 11:
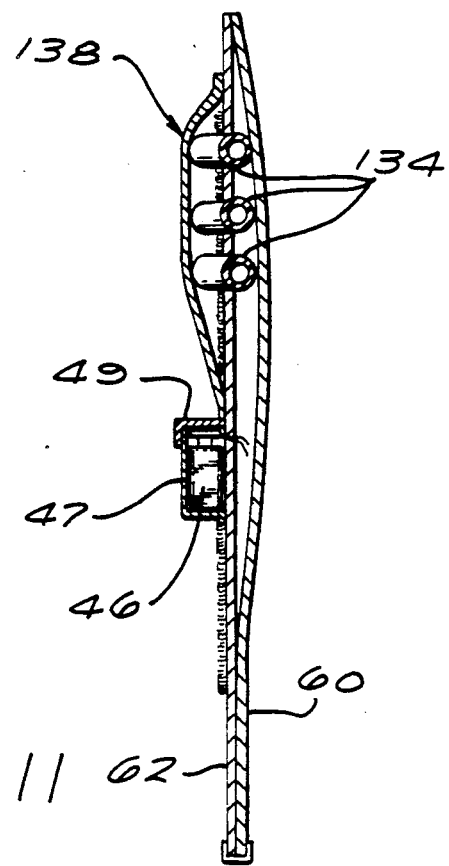
FIG. 11 is a cross section view taken along line 11—11 of FIG. 3.

The back support 10, in a further embodiment of the present invention may also include means 36 for heating the gel-like material 14 as best seen in FIGS. 4–5. In an exemplary embodiment of the present invention, heating means 36 may include a resistive type electrical heating element 38 disposed within the pad 12 and surrounded by the gel-like material 14, and means 40 for conducting external electric power to the heating element 38. As best seen in FIG. 4, conducting means 40 may, in one embodiment of the present invention, include a source 42 of DC voltage electrically coupled to the heating element 38 through a rheostat 44 and a switch 46. The DC voltage source 42, rheostat 44, the switch 46 and the heating element 38 are all serially coupled in a single current loop. In an alternative exemplary embodiment of the present invention, conducting means 40 may include a variable transformer 48 having a primary 50 and a secondary 52. The primary coil 50 is adapted for coupling to a source of AC power 54, such as a conventional wall outlet. The secondary coil 52 is electrically coupled to the heating element 38 through the series coupled switch 46. The variable transformer 48 is adjustable by the user 22 to regulate the current through the heating element 38 to regulate the heating of the gel-like material 14, similarly to the rheostat 44 described hereinabove. Switch 46 may be a conventional push button type secured by a structural support 49. A flap of material 49 may totally enclose the switch 46 but still allow activation thereof, as best seen in FIG. 11.

The supporting means 18 is a brace 58 constructed of an elastic fabric and generally dimensioned to fit around the lower torso of the user 22 to support the pad 12 adjacent the lower back 20 as hereinabove described. The brace 58 includes an inner surface 60, an outer surface 62, a first section 64, a second section 66 and a third section 68 intermediate the first section 64 and the second section 66. The brace 58 further includes means 70 for releasably attaching the first section 64 to the second section 66 when the brace 58 is stretched around the torso thereby supporting the pad 12 in firm engagement against the lower back 22. For example, attaching means 70 may be a loop and hook type fastener available under the VELCRO trademark.

The third section 68 is dimensioned to be positioned adjacent the lower back 20 of the user 22 and has a first pocket 72 adjacent the inner surface 60 and a second pocket 74 intermediate the first pocket 72 and the outer surface 62. The pad 12 is removably received by the first pocket 72. The air bladder 16 is removably received by the second pocket 74.

As best seen in FIG. 7, the, third section 68 of brace 58 includes a first sheet 76 and a second sheet 78 of elastic fabric in a facing relationship and being of sufficient thickness and strength to provide support when stretched adjacent the lower back 20. Each of the first sheet 76 and the second sheet 78 respectively have a lower edge 80, 81 an upper edge 82, 83 and a pair of lateral edges 84, 85, 86, 87. The first sheet 76 and the second sheet 78 are joined together at the respective lower edges 80, 81 and at selected points 88 along the lateral edges 84–87. The upper edge 82, 83 forms an opening 90 of the second pocket 74.

The third section 68 further includes a third sheet 92 of air permeable material such as a mesh type fabric in a facing relationship to the second sheet 78 and has a lower edge 94, an upper edge 96 and lateral edges 98, 100. The second sheet 78 and the third sheet 92 are joined together at the lower edge 81, 94 and at their respective lateral edges 85, 87, 98, 100. The upper edge 83, 96 of each of the second sheets 78 and third sheet 92 form an opening 102 of the first pocket 72. To keep the pad 12 within the first pocket 72, a loop and hook type fastener 104 commercially available under the VELCRO trademark, may be provided to keep the opening 102 closed.

It may be noted that the air bladder 16 is mounted on the inner side of the sheet 76 of elastic material, wherein sheet 76 has an inner side facing the user's body and an outer side facing away from the user. Also, gel pad 12 is mounted to the assembly with the air bladder 16 between the gel pad 12 and the inner side of the elastic sheet 76.

With particular reference to FIGS. 8–12, the air bladder 16 also includes means 106 for securing the bladder 16 within the second pocket 74. The securing means 106 includes a plurality of elongated straps 108 having a first end 110 and a second end 112. The first end 110 is affixed to the bladder 16. The straps 108 extend outwardly from the second pocket 74 between the selected points 88 along the lateral edges 84–87 of the first sheet 76 and second sheet 78. The second end 112 of the straps 108 are releasably attached to an adjacent one of the first section 64 and the second section 66 of the brace 58. More particularly, the straps 108 are attached to the outer surface 62 of the brace 58. The straps 108 are constructed of elastic material, similar to the brace 10. After the brace 10 has been tightened about the user 22, the straps 108 provide for further adjustment of the pressure exerted on the lower back 20.

The bladder 16 further has a first lateral edge 114 and a second lateral edge 116. The first end 110 of a first pair of the straps 108 are affixed to the first lateral edge 114 and the first end 110 of a second pair of the straps 108 are affixed to the second lateral edge 116.

As described hereinabove, the bladder 16 includes a plurality of chambers 26. More particularly, the chambers 26 include a first chamber 119 and a second chamber 120. The first chamber extends substantially between the first lateral edge 114 and a vertical midpoint 122 bisecting the bladder 16. The second chamber 120 extends substantially between the second lateral edge 116 and the midpoint 122. Chambers 26 may further include a third chamber 124 extending between the first lateral edge 114 and the second lateral edge 116 of the bladder 26 and between an upper edge 125 and a lower edge 127 of the bladder 26.

In one embodiment of the present invention, bladder 26 may include a first wall 126 a second wall 128 and a third wall 129 in a facing relationship to each other. The first wall 126 is sealed to the third wall 129 at selected locations to form the first and second chambers 119, 120. The second wall 128 and the third wall 130 are sealed together to form the third chamber 124. In one embodiment of the present invention, the first wall 126, the second wall 128 and third wall 129 may be constructed from Vinyl.

The first and second chambers 119, 120 occupy one side of the bladder 26 and the third chamber 124 is on the other side. The first and second chambers 119, 120 are also approximately two-thirds to three-fourths the height of the third chamber 124. The third chamber 124 has points 131 wherein the second wall 128 and the third wall 129 are sealed to each other to form intercommunicating cells 133. When inflated, the cells cause the bladder to assume an arcuate shape to conform to the lower back 20 and to exert a uniform force upon the gel pad 12, thereby pressing the gel pad 12 against the lower back 20. The first and second bladders 119, 120 are individually inflatable to adjust the pressure, somewhat laterally, against the lower back.

In one embodiment of the present invention, the inflating means 24 may include a valve assembly 130 which is carried by one of the first sections 64 and second section 66, as best seen in FIG. 6. The valve assembly includes the one-way valves 28 hereinabove described. Valve assembly further includes the plurality of pressure relief valves 132. Each of the pressure relief valves 132. Each of the pressure relief valves 132 is associated with an outlet 32 of a respective one of the one-way valves 28. The pressure relief valves are user activated to release pressure of respective one of the chambers 26. To operatively connect the outlet 32 to the respective one of the chambers 26, a tube 134 may be fitted over the outlet 32 and coupled to a fitting 136 mounted through either the first walls 126 or second wall 128 of the bladder 26 to communicate with the respective one of the first chamber 118, second chamber 120 or third chamber 124. A support structure 138 may be attached to the outer surface 62 of the first 64 to carry the valve assembly 130 and parts of the tubes 134.

There has been described above an exemplary preferred embodiment of a novel back brace. It should be apparent that those skilled in the art may now make numerous usage of and departures from the above-described exemplary embodiment without departing from the inventive concepts described herein. Accordingly, the present invention is to be defined solely by the scope of the following claims.

What is claimed is:

1. A back support comprising:
   a brace constructed of elastic fabric and generally dimensioned to fit around a lower torso of a user, said brace including an inner surface, an outer surface, a first section, a second section, a third section intermediate said first section and said second section, and means for releasably attaching said first section to said second section when said brace is stretched around said torso, said third section being adapted for positioning adjacent a lower back of a user, said third section having a first pocket adjacent said inner surface and a second pocket intermediate said first pocket and said outer surface;
   a pad of gel-like material removably received by said first pocket;
   an air bladder generally co-extensive with said pad, said bladder being removably received by said second pocket; and
   means for inflating said air bladder to press said pad against said lower back.

2. A back support as set forth in claim 1 wherein said third section includes:
   a first sheet and a second sheet of elastic fabric in a facing relationship and being of sufficient thickness and strength to provide support when stretched adjacent said lower back, each of said first sheet and said second sheet having a lower edge, an upper edge and lateral edges, said first sheet and said second sheet being joined together at said lower edge of each said sheet and at selected points along said lateral edges of each said sheet, said upper edge of each of said first sheet and said second sheet forming an opening of said second pocket; and
   a third sheet of air permeable material in a facing relationship to said second sheet having a lower edge, an upper edge and lateral edges, said second sheet and said third sheet being joined together at said lower edge of said second sheet and said third sheet and said lateral edges of said second sheet and said third sheet, said upper edge of each of said second sheet and said third sheet forming an opening of said first pocket.

3. A back support as set forth in claim 2 wherein said air bladder includes:
   means for securing said bladder within said second pocket.

4. A back support as set forth in claim 3 wherein said securing means includes;
   a plurality of elongated straps having a first end and a second end, said first end of said straps being affixed to said bladder, said straps extending outwardly of said second pocket between said selected points along said lateral edges of said first sheet and said second sheet, said second end of said straps being releasably attached to an adjacent one of said first section and said second section of said brace.

5. A back support as set forth in claim 4 wherein said second end of said straps are attached to said outer surface of said brace.

6. A back support as set forth in claim 5 wherein said bladder has a first lateral edge and a second lateral edge, said first end of a first pair of said straps being affixed to said first lateral edge, said first end of a second pair of said straps being affixed to said second lateral edge.

7. A back support as set forth in claim 6 wherein said bladder includes a plurality of chambers, each of said chambers being individually inflatable by said inflating means.

8. A back support as set forth in claim 7 wherein said chambers include a first chamber and a second chamber, said first chamber extending substantially between said first lateral edge and a vertical midpoint of said bladder, said second chamber extending substantially between said second lateral edge and said vertical midpoint.

9. A back support as set forth in claim 8 wherein said chambers further include a third chamber extending between said first lateral edge and said second lateral and further between an upper edge and a lower edge of said bladder, said first chamber and said second chamber being less than the height of said third chamber.

10. A back support as set forth in claim 9 wherein said bladder includes a first wall a second wall and a third wall in a facing relationship to each other, said first wall being sealed to said third wall at selected locations to form said first chamber and said second chamber, said second wall being sealed to said third wall at selected locations to form said third chamber.

11. A back support as set forth in claim 10 wherein said walls are constructed from vinyl.

12. A back support as set forth in claim 7 wherein said inflating means includes:

a valve assembly carried by either one of said first section and said second section, said valve assembly having a plurality of one-way valves, each of said one-way valves having an outlet operatively communicating with the respective one of said chambers and an inlet; and an air pump adapted for coupling to said inlet of a user selected one of said one-way valves.

13. A back support as set forth in claim 12 wherein said valve assembly further includes a plurality of pressure relief valves, each of said pressure relief valves being associated with said outlet of a respective one of one-way valves, said pressure relief valves being user activated to release pressure from a respective one of said chambers.

14. A back support comprising:

a brace constructed of elastic sheet material and generally dimensioned to fit around the lower torso of the user, said brace including a first section, second section, at third section intermediate said first section and said second sections said third section including said elastic sheet material having an inner side and an outer side, and being positionable adjacent the lower back of a user; and said first and second sections extending from said third section to encompass the user's body, and means for releasably attaching said first section to said second section toward the front of the user's body when said brace is stretched around said torso;

an air bladder;

means for mounting said air bladder within said third section and adjacent said inner side of said elastic sheet material;

a gel pad;

means for mounting said gel pad adjacent said air bladder with said air bladder interposed between said inner side of said elastic sheet material and said gel pad, so that said gel pad is positioned adjacent said lower back, said gel pad and said air bladder being generally co-extensive with each other; and means for inflating said air bladder to press said pad against said lower back;

whereby said elastic fabric and said air bladder, following inflation thereof, press said gel pad firmly against the user's lower back.

15. A back support as defined inn claim 14 further comprising straps secured to said air bladder and extending through openings in said elastic sheet material and being secured to the outer side thereof to hold said air bladder against the inner side of said elastic sheet material.

16. A back support as defined in claim 14 wherein said air bladder includes a plurality of chambers, each of said chambers being individually inflatable by said inflating means.

17. A back support as defined in claim 14 wherein said air bladder includes at least three chambers, with two of said chambers being mounted side by side with one another, and a third chamber overlying said two chambers.

* * * * *